United States Patent [19]

Crosby et al.

[11] 4,025,535
[45] May 24, 1977

[54] SULFOALKYLATED FLAVANONE SWEETENERS

[75] Inventors: Guy A. Crosby; Grant E. DuBois; Ned M. Weinshenker, all of Palo Alto, Calif.

[73] Assignee: Dynapol Corporation, Palo Alto, Calif.

[22] Filed: Feb. 13, 1976

[21] Appl. No.: 657,905

Related U.S. Application Data

[63] Continuation-in-part of Ser. No. 561,522, March 24, 1975, Pat. No. 3,974,299.

[52] U.S. Cl. .............................. 260/345.2; 426/548; 260/326.8 H; 260/429 K; 260/429.9; 260/438.1; 260/439 R; 260/448 R; 260/511; 260/590 D; 260/607 R
[51] Int. Cl.² ....................................... C07D 311/02
[58] Field of Search ........................ 260/345.2, 511

[56] References Cited
UNITED STATES PATENTS

| | | | |
|---|---|---|---|
| 3,495,009 | 2/1970 | Tronche | 260/345.2 |
| 3,598,840 | 8/1971 | Majoie | 260/345.2 |
| 3,812,156 | 5/1974 | Bonola et al. | 260/345.2 |

*Primary Examiner*—Bernard Helfin
*Assistant Examiner*—Nicky Chan
*Attorney, Agent, or Firm*—William H. Benz

[57] ABSTRACT

Flavanones represented by the formula

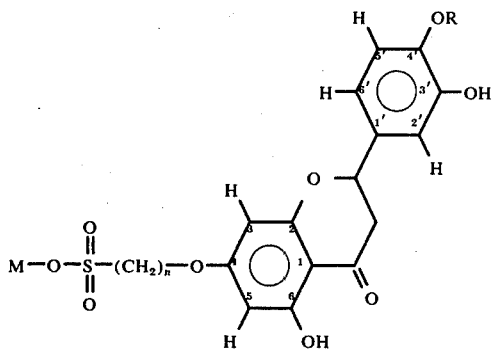

wherein R is a lower alkyl of from one to three carbon atoms inclusive, $n$ is an integer of from one to three inclusive and M is hydrogen or a physiologically acceptable metal cation, are disclosed. These materials are themselves useful as dietetic sweeteners as well as being direct intermediates for the preparation of useful dihydrochalcone sweeteners.

16 Claims, No Drawings

SULFOALKYLATED FLAVANONE SWEETENERS

Reference TO RELATED APPLICATION

This is a continuation-in-part of copending U.S. patent application Ser. No. 561,522, filed Mar. 24, 1975, now U.S. Pat. No. 3,974,299, issued Aug. 10, 1976.

BACKGROUND OF THE INVENTION

This invention relates to flavanone compounds. More particularly, it relates to a limited class of sulfonate-group-containing flavanones.

Flavanones have been known since the nineteenth century. They occur in nature and have been synthesized in the laboratory. They are known to enter into a wide range of chemical reactions. In one reaction sequence, they can be isomerized with base to give chalcones which can then be hydrogenated to yield dihydrochalcones. This sequence is exemplified by the following conversion of the naturally occurring flavanone, naringin, to naringin dihydrochalcone:

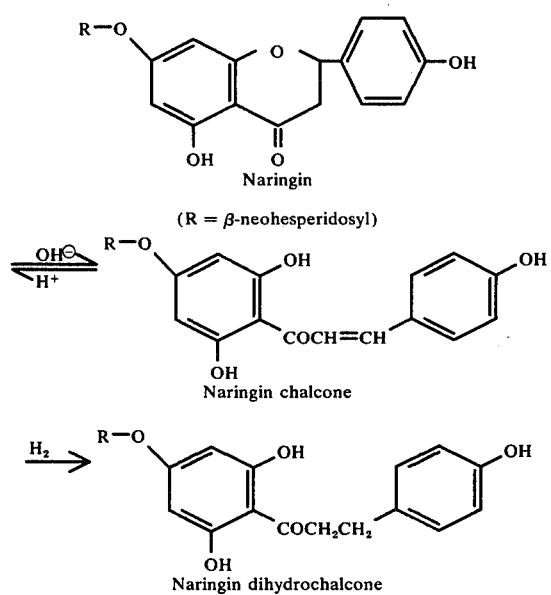

Flavanones and their conversion to dihydrochalcones took on special interest in the early nineteen-sixties when it was discovered that dihydrochalcones formed from the flavanones prunin, naringin, and neohesperidin were intensely sweet. These flavanones which in the art gave sweet dihydrochalcones may be chemically characterized as having large glycoside residues attached via an oxygen bond links to their left most aromatic rings. I.e., R in the above formulae is a glycoside such as $\beta$-neohesperidosyl, $\beta$-rutinosyl or the like. While they yield sweet dihydrochalcones, such flavanones themselves are generally bitter or tasteless. In fact, naringin (the principle bitter compound in grapefruit rind) finds commercial application as a bittering agent in some tonic water formulations. Horowitz, in Chapter 14 of *Biochemistry of Phenolic Compounds*, Harborne Ed., (Academic Press, 1964) pages 555–556 reports that, aside from one material, hesperetin, which has slight sweetness, flavanones useful as dihydrochalcone sweetener precursors which he examined were tasteless or bitter. Similar results are reported by Horowitz and Gentile at *Agr. and Food Chem.* Volume 17, No. 4 p. 696 (1969) and by Kamiya et al at *Agr. Biol. Chem.* Volume 39, p. 1757 (1975).

STATEMENT OF THE INVENTION

We have now discovered a new class of flavanones which yield intensely sweet dihydrochalcones. These new compounds are represented by General Structural Formula (I)

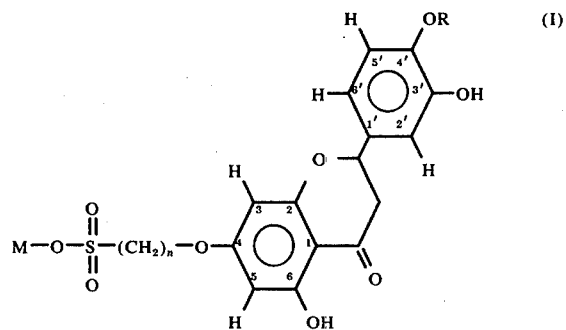

wherein R is a lower alkyl of from one to three carbon atoms inclusive, $n$ is an integer of from one to three inclusive and M is hydrogen or a physiologically acceptable metal cation. These flavanones are characterized by an absence of glycoside residues in their structure and by the substantial water-solubility of their corresponding dihydrochalcones represented by General Structural Formula II (which property is difficult to achieve and important to successful application as sweeteners).

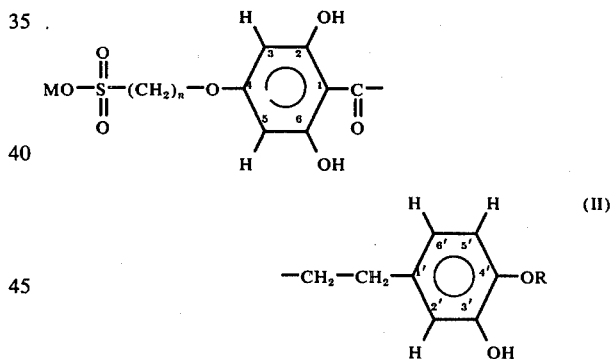

These flavanones are further characterized by the most surprising property of being intensely sweet themselves - having sweetening powers as much as several hundred times that of sucrose. To our knowledge, the compounds are the first intensely sweet flavanones ever disclosed.

DETAILED DESCRIPTION OF THE INVENTION

The Flavanones

In this Detailed Description, references will repeatedly be made to the positions of various substituents on the flavanone and dihydrochalcone molecules. These positions are numbered and will be referenced in accordance with General Formulae (I) and (II).

The flavanones of this invention contain two hydroxyl groups at the 6 and 3' positions. They contain hydrogens at the 3, 5, 2', 5', and 6' positions. At the 4' position they contain a lower saturated alkoxy group of from one to thre carbon atoms, that is one selected from the group of methoxy, ethoxy and the propoxies; preferably the 4'-substituent is a methoxy or n-propoxy, and most preferably a methoxy. At the 4 position they contain a substituted oxy group. This oxygen atom is substituted with an alkyl sulfonate anion to yield an oxyalkylsulfonate anion of from one to three carbon atoms inclusive. The alkyl sulfonate anion is present as the acid or a salt with a physiologically acceptable metal cation. As used herein, a "physiologically acceptable metal cation" is defined to include $Li^+$ and the cations of the third and fourth period metals which are nontoxic, i.e., $Na^+$, $K^+$, $Mg^{+2}$, $Ca^{+2}$, $Al^{+3}$, $Mn^{+2}$, $Fe^{+3}$, $Cu^{+2}$ and $Zn^{+2}$. Preferred metal cations are the cations of the third and fourth period group I and II metals, i.e., $Na^+$, $K^+$, $Mg^{+2}$ and $Ca^{+2}$.

Preparation of Flavanones

The materials of General Formula I are conveniently formed in a general sense, by the mechanism of alkylating the 4-hydroxyl group of the natural product hesperetin

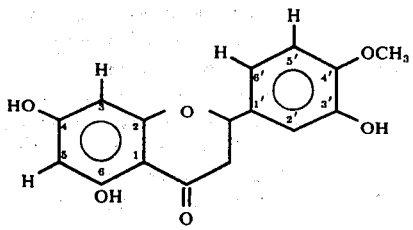

(or a 4'-ethoxy or propoxy equivalent of hesperetin) with a one to three carbon alkyl sulfonate group. The 4-ethoxy or propoxy equivalent of hesperetin can be conveniently prepared by the Aldol condensation of phloroacetophenone with the appropriate 4-alkoxy-3-hydroxy-benzaldehyde, followed by acid catalyzed cyclization of the resulting chalcone.

In the case when n in General formula I equals 1, sodium iodomethanesulfonate or the pyrrolidine amide of chloromethylsulfonic acid are suitable agents with which to effect alkylation. More specifically, by the first route hesperetin or a 4'-ethoxy or methoxy equivalent can be reacted with the sodium salt of iodomethanesulfonic acid in the presence of potassium carbonate in DMF at reflux for several hours to yield at the 4 position of the hesperetin (or its equivalent) a sulfo-substituted methoxy. In the second route, chloromethylsulfenyl chloride is first prepared by contacting trithiane,

with molecular chlorine. The chloromethylsulfenyl chloride can then be reacted with pyrrolidine,

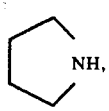

to form

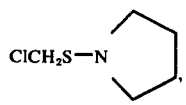

which will facilely alkylate hesperetin (or the 4' ethoxy or propoxy equivalent) in the 4 position and, after S oxidation and sulfonamide hydrolysis, yields the desired sulfomethoxy flavanone.

In the case where n in General Formula I equals 2, the alkylating agent can be $Br-CH_2-CH_2-SO_3^-Na^+$, or the like. This material, when contacted with an equimolar amount of hesperetin (or a 4' ethoxy or propoxy equivalent) in the presence of potassium carbonate or a similar weak base, in DMF, DMXO, or the like, preferentially alkylates the 4-hydroxyl. There is, of course, as with all these reactions, some alkylation of other hydroxyls. The various materials may be separated and the desired 4-alkylate recovered by fractional crystallization of chromatography techniques.

In the case where n in General Formula I equals 3, propane sultone is the alkylating agent of choice, as it directly attaches the required three carbon alkyl group and the $SO_3^-$ in one step. This alkylation is carried out in DMF or DMSO or an equivalent dipolar aprotic solvent in the presence of sodium carbonate or a like weak base.

All of these alkylations can be carried out under relatively mild conditions, such as about room temperature for 24 to 72 hours. It is also possible to use elevated temperatures, such as up to about 100° C with corresponding shorter reaction times such as as short as about 1 hour.

As above noted, in one use the present flavanones are converted to dihydrochalcones by ring opening and reduction.

The ring opening and reduction may be carried out in two steps — opening and then hydrogenating. The opening is brought about by contacting the alkylation product with a relatively strong base such as an aqueous alkali metal hydroxide solution for 0.2 to 4 hours at 10° to 100° C. The hydrogenation can be carried out with hydrogen gas and a hydrogenation catalyst such as a supported noble metal (e.g., platinum or palladium) catalyst or a nickel catalyst or the like at a temperature of from 10° to 100° C for from 0.5 to 24 hours. Preferably the reduction and opening are carried out simultaneously with base, catalyst and hydrogen being present at once.

The products of any of these reactions can be purified and isolated by fractional crystallization, thin layer chromatography and the like, as desired.

The preparative schemes set forth above depict sodium as the cation. By varying starting materials among potassium, calcium and the like salts, a variety of metal cations can be incorporated. Treatment with $H^+$ can yield the acid. Also, it is possible to change cations by passage of a solution of flavanone over an appropriately charged ion exchange resin or often by merely adding an excess of the desired cation to a solution of flavanone and precipitating the desired salt.

These preparations will be further set forth in the examples. These are not intended to be limiting as other methods equivalent to those skilled in the art of organic synthesis may be employed as well.

Use of the Flavanone

These flavanones find use as chemical intermediates in the preparation of certain sweet and water soluble 4-sulfonate-alkoxy-substituted dihydrochalcones. (The term "water soluble" as used throughout this application is defined to mean a solubility in neutral room temperature water of not less than 1000 parts per million by weight.) This use has been described above and will be shown in the Examples.

The flavanones most surprisingly themselves also find application as sweeteners of consummable materials. In this use they are admixed with edible materials such as foods, beverages, medicines, and the like, in amounts effective for affording the degree of sweetness desired.

The flavanones represented by Formula I can be prepared in a variety of forms suitable for the utilization of sweetening agents. Typical forms which can be employed are: solid forms such as powders, tablets, and granules; and liquid forms such as solutions, suspensions, syrups, and emulsions. These forms can consist of the compounds of Formula I apart from or in association with nontoxic sweetening agent carriers, i.e., nontoxic substances commonly employed in association with sweetening agents. Such suitable carriers include liquids such as water, ethanol, sorbitol, glycerol, citric acid, corn oil, peanut oil, soybean oil, sesame oil, propylene glycol, corn syrup, maple syrup, and liquid paraffin; and solids such as lactose, cellulose, starch, dextrin and other modified starches, calcium phosphate and calcium sulfate. Obviously incompatible for use with the sweetening agents of Formula I would be toxic carriers such as methanol and dimethyl sulfoxide.

The flavanones are added to the edible composition by mixing methods known in the art. They may be used alone or as the primary or secondary sweetener in the final composition; with a natural sweetener such as sucrose, or another synthetic sweetener such as saccharin or cyclamate also being added. Combinations of two or more of the present flavanones may be used, if desired.

Examples of specific edible materials which can be sweetened by the addition of a flavanone of Formula I or by a novel combination of the material of Formula I with a known sweetening agent include: fruits, vegetables, and juices; meat products such a bacon and sausage; egg products; fruit concentrates; gelatins and gelatin-like products such as jelly and preserves; milk products such as ice cream, sour cream and sherbet; icings; syrups; grain products such as bread, cereals, pasta and cake mixes; fish; cheese products; nut products; beverages such as coffee, tea, noncarbonated and carbonated soft drinks, beers, wines and liquors; and confections such as candy and chewing gums.

Additional illustrations of the type of commercial products in which the sweetening agents or combinations thereof with known sweetening agents can be used are granulated mixes which upon reconstitution with water provide noncarbonated drinks; instant pudding mixes; instant coffee and tea; pet foods; livestock feed; tobacco and consumable toiletries such as mouth washes and toothpastes, as well as proprietary and nonproprietary pharmaceutical preparations.

The amount of flavanone employed can vary widely, just as the amount of natural sugar sweetener employed varies from person to person and food application to food application. As a general rule, the weight of flavanone added will be about 1/50–1/500th the weight of sucrose required to yield the same sweetness. Thus, additions of from about 0.002% up to about 1.00% by weight (basis edible substance) may be usefully employed. The present materials offer the advantage that their substantial water solubility permits such addition to most food systems.

These flavanones, their preparation and their use are further described in the following Examples. These are to illustrate the invention and not to be construed as limitations on this invention, which is instead defined by the appended claims.

EXAMPLE I

A. Preparation of

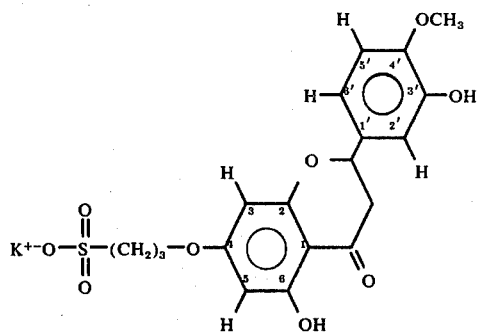

To a solution of 3.02 g (10.0 mmoles) of hesperetin and 2.44 g (20 mmoles) of propane sultone in 40 ml DMF is added 1.38 g (10.0 mmoles) of anhydrous $K_2CO_3$. The resulting reaction mixxture is stirred at ambient temperature for about 20 hrs. The reaction is then checked by tlc (Eastman Chromagram 13254 Cellulose, HOAc-$H_2$O-i-BuOH 1:1:2) and found to contain mainly one product ($I_2$ staining and uv visualization) having $R_f$=0.68 along with a small amount of starting material. The DMF is then removed at reduced pressure and the residue taken up in 25 ml water. This mixture is then extracted with EtOAc (4 × 15 ml) to remove unreacted hesperetin and propane sultone. The aqueous solution is then concentrated to yield the desired flavanone alkylation product as an off-white solid which can be purified by recrystallization from water.

B. Use of the Flavanone.

A portion of the product of Part A is dissolved in 100 ml of 5% KOH and transferred to a hydrogenation vessel. Then 1 g of 5% palladium on charcoal is added, the mixture is flushed with argon, and then with hydrogen. Finally, it is pressured to 24 psig with hydrogen and shaken overnight. The mixture is filtered through Celite and brought to about pH 7–8 with dilute hydrochloric acid.

The resultant solution is concentrated to a volume of ca. 150 ml and allowed to stand overnight, whereupon 1.46 g of white clusters separates. Concentrates of the mother liquor yield an additional 1.17 g of material for a total yield of 2.63 g (55%). Tlc analysis (as above) of this product indicates only one component having a $R_f$=0.67 and which has spectra and elemental analyses consistent with the product

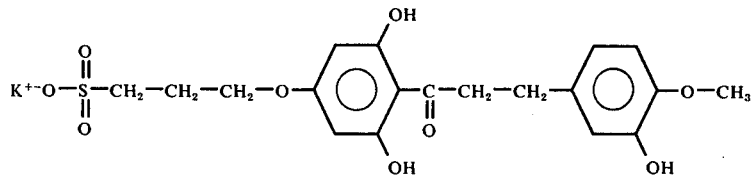

An additional portion of the product made in accordance with Part A is dissolved in water at a 400ppm concentration. It is tasted by a group of volunteers who report that it has sweetness equivalent to that of a 85,000 ppm sucrose solution and that in flavor character it is very sugar-like. This would indicate a sweetening power of 200–300 times sucrose.

EXAMPLE II

A. Preparation of

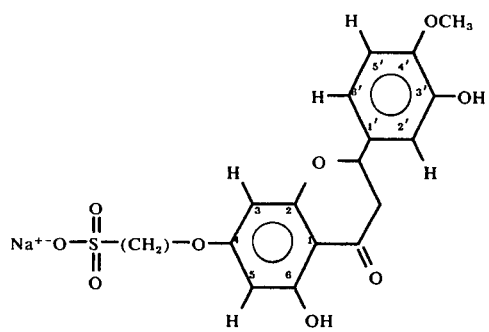

Following the general teachings of Douglass et al., *J. Org. Chem.* 15, 795–9 (1950), purified trithiane,

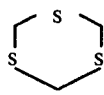

28 grams, and methylene chloride reaction solvent are placed in a vessel and chilled to 0° C. Chlorine gas (16 grams) is slowly passed into the vessel with stirring while maintaining the 0° C temperature. After three hours, the vessel is permitted to warm to room temperature and unreacted chlorine is removed.

The reaction mixture is warmed to about 50° C and vacuum is applied, causing chloromethylsulfenyl chloride ($ClCH_2SCl$) to distill overhead.

Chloromethylsulfenyl chloride (one equivalent) is dissolved in benzene and two equivalents of pyrrolidine is gradually added with stirring. The mixture is stirred at room temperature for one hour. Benzene is stripped and a product

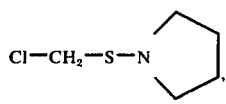

(A), is isolated by distillation.

A solution of 3.0 g of hesperetin (Sigma Chemical Co.) in 20 ml of dimethylformamide is prepared. 0.7 Grams of anhydrous potassium bicarbonate is added followed by 4.6 g of (A). The mixture is stirred overnight at which time excess peracetic acid is added in acetic acid solvent and stirred for 12 hours to form

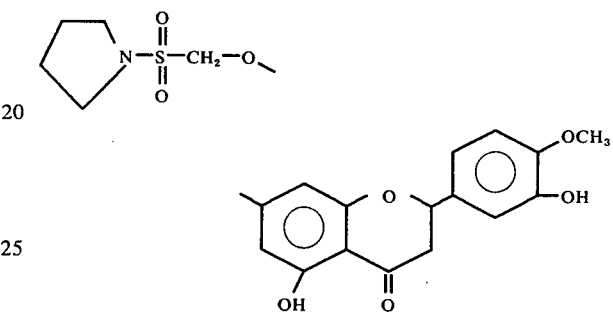

Water is then added and the mixture is stirred at room temperature for an hour to oxidatively hydrolyze and convert the sulfonamide to the flavanone sulfonate,

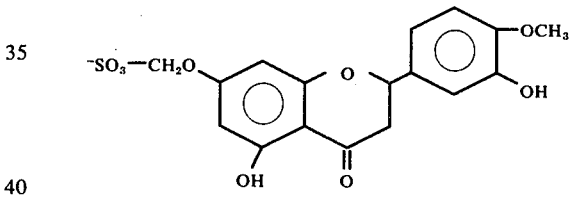

Sodium bisulfite is added to consume unreacted peracetic acid. Following evaporation of volatile materials, the flavanone sulfonate as the sodium salt is obtained pure by crystallization from water.

B. Use of the Flavanone.

In a first use, an aqueous solution of the flavanone (400ppm) is prepared and tasted and found to be sweet. The flavanone is then added (400 ppm) to a soft drink base, to a chewing gum and a toothpaste. It sweetens these materials.

In a second use, the sulfonate (1.5 grams) is dissolved in 30 ml of 5% aqueous KOH and placed in a 250 ml reaction flask with 250 mg of 5% palladium on charcoal. The reaction at room temperature and about atmospheric pressure for about 35 hours. Thin layer chromatography analysis of the mixture before and after reaction indicates that there has been essentially quantitative reduction and opening of the flavanone ring to yield the dihydrochalcone

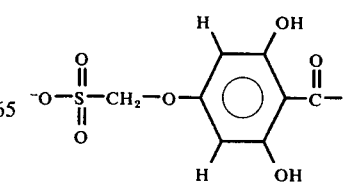

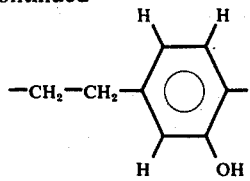

as the potassium salt.

This material is isolated following neutralization to pH 7-8 with HCl by concentration of the resultant solution in vacuo. After purification by recrystallization, analysis by NMR indicates that the producer is the one compound.

EXAMPLE III

A. Preparation of

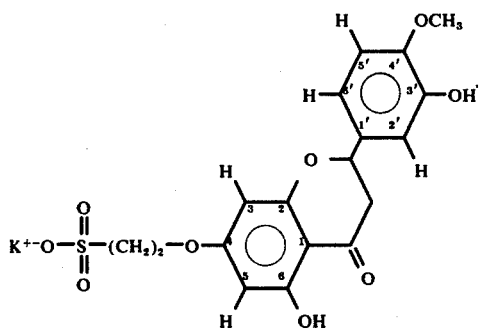

72 Milligrams of 50% sodium hydride is washed with hwxane. Seven milliliters of anhydrous dimethylsulfoxide is added under an argon cap. Next, 302 mg of hesperetin is slowly added in about one ml of dimethylsulfoxide. The mixture is reacted at room temperature and then at 50° C for about an hour. Then Br-CH$_2$-CH$_2$-SO$_3$Na (253 mg) in dimethylsulfoxide is added and the mixture is stirred overnight under argon at room temperature. Solvent is then stripped off and the product is extracted with ethylacetate. The desired flavanone is crystallized from water to purify.

B. Use of the Flavanone.

The material of Part A is dissolved in a cola beverage base, dispensed in a gelatin dessert mix and added to fruit preserves. In each application it increases the sweetness of the edible material.

EXAMPLE IV

This example deals with the preparation of additional metal ion salts of the flavanones.

A sample of the propoxysulfonate flavanone potassium salt prepared in Part A of Example I is placed on an anion exchange column such as the polyalkylamonium chloride column marketed as Bio Rex 5. Elution is begun with a 1:1:1 acetonitrite-ethanol-water mixture. Then a gradient of 1 molar aqueous lithium chloride is added. This causes the lithium salt of the propoxysulfonate flavanone to elute. The lithium sulfonate salt is recovered from the eluent by crystallization. This procedure is repeated using sodium chloride and the methoxy and methoxy flavanones of Examples II and III with equivalent results.

EXAMPLE V

This example deals with the preparation of alkaline earth metal salts of the flavanones. Basically, it involves adding an excess of the alkaline earth cation to a solution of the flavanones and separating the alkaline earth metal salt by crystallization.

An aqueous solution of the flavanone potassium salt prepared in Example I is prepared. A saturated solution of calcium chloride is added. The combined solution is evaporated until crystals form. These are the calcium salt of the flavanone prepared in Example I.

EXAMPLE VI

This example deals with the preparation of the free acids of the flavanones (i.e., when M equals hydrogen).

A solution of the potassium salt of the flavanone of Example I is prepared and placed on a strongly acidic cation exchange resin column such as Rohm and Haas Amberlite IR-120 strongly acidic sulfonated polystyrene. Aqueous hydrochloric acid is passed over the column and the eluent is collected. The eluent is freeze-dyed to remove all water and residual hydrochloric acid and to yield the desired free acid as a solid product.

EXAMPLE VII

This example sets forth the preparation of 4'-ethoxy and propoxy equivalents of the flavanone of Example I. These materials are formed by condensing the appropriate benzaldehydes and acetophenones to chalcones and then cyclyzing under acidic conditions to flavanones.

A. Preparation of the acetophenone.

To a solution of 1.68 g of phloroacetophenone and 12.7 g of benzyl chloride in 20 ml of DMF is added 5.53 g of anhydrous K$_2$CO$_3$. The mixture is stirred for 16 hours at 65° under argon. The mixture is diluted with 100 ml of 5% NaCl and extracted with ethyl acetate (2 × 50ml). The extracts are washed with 5% NaCl and 2% NaOH, dried over MgSO$_4$ and concentrated to a red oil which is purified on a dry 250 g silica gel columning CCl$_4$ as eluent. This yields 2,4,6-tribenzyloxyacetophenone as a yellow oil.

B. Preparation of aldehydes.

To a solution of 14.2 g of 3,4-dihydroxybenzaldehyde, 10.9 g of ethyl bromide, and 14.98 g sodium iodide in 150 ml DMF is added 13.82 g of anhydrous K$_2$CO$_3$. After 16 hours at R.T., tlc and VPC analyses indicate substantial completion of reaction.

The reaction mixture is then diluted with 500 ml 5% NaCl solution and extracted with ether (2 × 250 ml). The combined ether extracts are washed with 5% NaCl solution and then with 5% NaOH solution. The combined base extracts are acidified with concentrated HCl while cooling in an ice bath. After standing overnight at 0°, a brown precipitate is filtered and washed with water. Recrystallization from EtOH-H$_2$O yields 3-hydroxy-4-ethoxy-benzaldehyde as off-white needles.

To a solution of 1.66 g of 3-hydroxy-4-ethoxy-benzaldehyde and 2.53 g of benzyl chloride in 20 ml DMF is added 2.76 g (20 mmoles) of anhydrous K$_2$CO$_3$. After stirring under argon for 21 hours, the reaction is checked by tlc and found to be complete. The reaction mixture is diluted with 60 ml 5% NaCl solution and extracted with EtOAc 50 ml. The combined extracts are washed with 5% NaCl solution, 1% NaOH solution, dried over MgSO$_4$ and concentrated yielding a yellow oil. After removal of volatile components at reduced pressure, the residue is recrystallized from aqueous ethanol yielding white needles of 3-benzyloxy-4-ethoxybenzaldehyde.

This aldehyde preparation is essentially repeated substituting n-propyl iodide for ethyl iodide in the starting materials. This results in 3-benzyloxy-4-n-propoxybenzaldehyde as a second aldehyde product.

C. Preparation of chalcones.

To a solution of 2.19 g of 2,4,6-tribenzyloxyacetophenone and 1.28 g of 3-benzyloxy-4-ethoxybenzaldehyde in 5.0 ml warm absolute ethanol is added 7.5 ml of 60% KOH. The resulting reaction mixture is stirred at ambient temperature overnight resulting in the formation of a gummy precipitate. The reaction mixture is then dumped into 30 ml of water and extracted with ether (2 × 25 ml), the combined portions of which are dried over MgSO$_4$ and concentrated yielding a yellow solid. Tlc analysis indicates the formation of a sole product and complete consumption of both starting materials. Recrystallization from EtOAc-MeOH yields yellow needles of 2,4,6,3'-tetrabenzyloxy-4'-ethoxychalcone, i.e.,

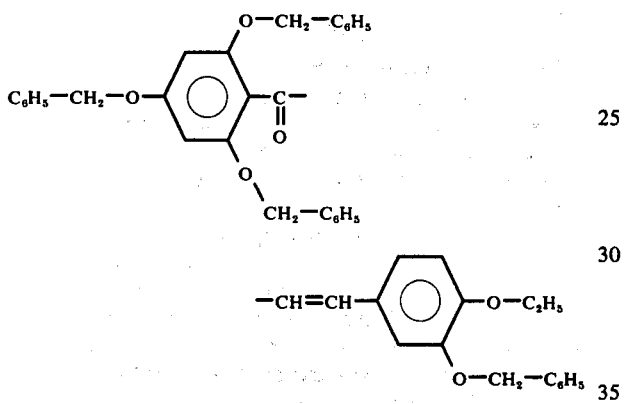

This reaction is repeated using the propoxy aldehyde in place of the ethoxy aldehyde. The product with results is the corresponding 4'-propoxychalcone.

D. Cyclization to flavanones.

To a solution of 1.35 g of the ethoxy chalcone of Part C in 20 ml of acetic acid is added 5.45 g of 47% (w) hydroiodic acid. The mixture is stirred at room temperature for 24 hours and then dumped into 45 ml of water and extracted with EtOAc (3 × 25 ml). The combined extracts are washed with water (6 × 100 ml) and concentrated to dryness. The resulting flavanone product,

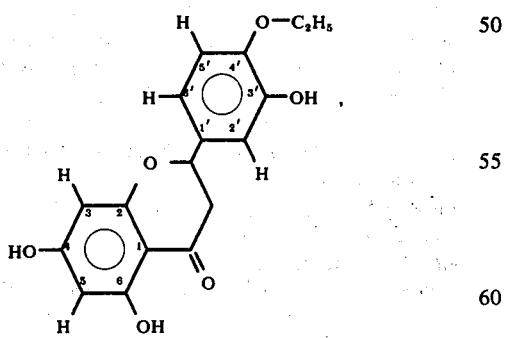

is recovered and purified by recrystallization from ethanol-water.

When this reaction is repeated using the 4'-propoxy chalcone of Part C the corresponding 4'-propoxy flavanone results.

E. Alkylation.

The two flavanones of Part D are serially substituted for hesperetin in the reaction and work-up of Part A of Example I. This results in the formation and recovery of first the 4'-ethoxy equivalent of the product of Example I and second the 4'-n-propoxy equivalent of the product of Example I, i.e.,

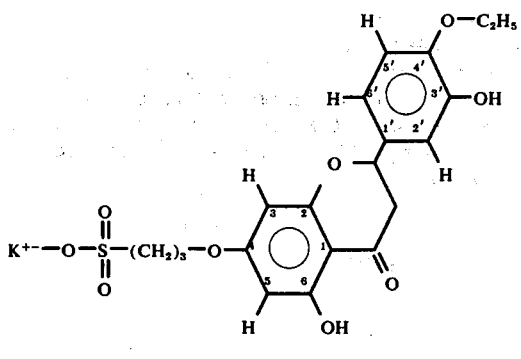

and

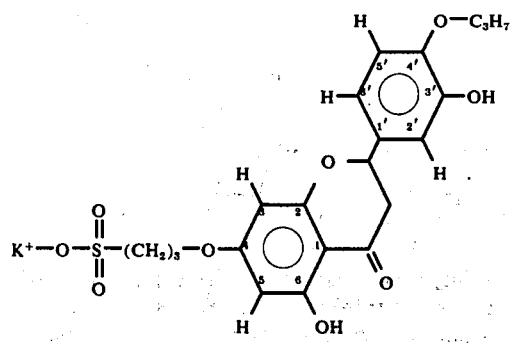

It will be apparent to those skilled in the art to likewise substitute the two flavanones of Part D of this example in the preparations of Examples II and III and the reactions of Examples IV, V and VI.

We claim

1. A flavanone compound represented by the structural formula

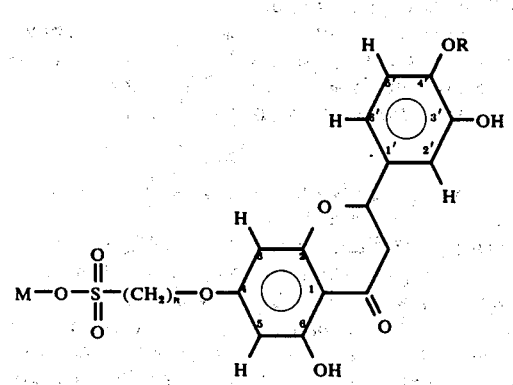

wherein R is a lower alkyl of from one to three carbon atoms inclusive, n is an integer of from one to three inclusive and M is hydrogen or a physiologically acceptable metal cation.

2. The compound of claim 1, wherein n has a value of 1 and R is methyl.

3. The compound of claim 1, wherein n has a value of 1 and R is ethyl.

4. The compound of claim 1, wherein n has a value of 1 and R is n-propyl.

5. The compound of claim 1, wherein $n$ has a value of 2 and R is methyl.

6. The compound of claim 1, wherein $n$ has a value of 2 and R is ethyl.

7. The compound of claim 1, wherein $n$ has a value of 2 and R is n-propyl.

8. The compound of claim 1, wherein $n$ has a value of 3 and R is methyl.

9. The compound of claim 1, wherein $n$ has a value of 3 and R is ethyl.

10. The compound of claim 1, wherein $n$ has a value of 3 and R is n-propyl.

11. The compound of claim 2, wherein M is potassium ion.

12. The compound of claim 2, wherein M is calcium ion.

13. The compound of claim 5, wherein M is potassium ion.

14. The compound of claim 5, wherein M is calcium ion.

15. The compound of claim 8, wherein M is potassium ion.

16. The compound of claim 8, wherein M is calcium ion.

* * * * *